(12) United States Patent
Park et al.

(10) Patent No.: US 11,714,071 B2
(45) Date of Patent: Aug. 1, 2023

(54) METHOD AND SYSTEM FOR INSPECTING GROWTH QUALITY OF GRAPHENE

(71) Applicant: HANWHA AEROSPACE CO., LTD., Changwon-si (KR)

(72) Inventors: Jin Sung Park, Changwon-si (KR); Jin Ho Jang, Changwon-si (KR)

(73) Assignee: Versarien PLC, Gloucestershire (GB)

( * ) Notice: Subject to any disclaimer, the term of this patent is extended or adjusted under 35 U.S.C. 154(b) by 56 days.

(21) Appl. No.: 16/883,025

(22) Filed: May 26, 2020

(65) Prior Publication Data
US 2021/0190741 A1    Jun. 24, 2021

(30) Foreign Application Priority Data
Dec. 24, 2019 (KR) ................ 10-2019-0174293

(51) Int. Cl.
  *G01N 31/00* (2006.01)
  *C23C 16/26* (2006.01)
  *G01N 33/38* (2006.01)

(52) U.S. Cl.
  CPC .......... *G01N 31/005* (2013.01); *C23C 16/26* (2013.01); *G01N 33/38* (2013.01)

(58) Field of Classification Search
  None
  See application file for complete search history.

(56) References Cited

U.S. PATENT DOCUMENTS 5,047,851 A * 9/1991 Sauerwein ............. G01N 21/93
382/149

FOREIGN PATENT DOCUMENTS

| JP | 2008-131025 A | 6/2008 |
| JP | 4427421 B2 | 3/2010 |
| KR | 10-1615117 B1 | 4/2016 |
| KR | 10-2016-0090141 A | 7/2016 |
| KR | 10-2017-0007135 A | 1/2017 |
| KR | 10-1768366 B1 | 8/2017 |

OTHER PUBLICATIONS

Machine Translation of KR20170007135A (Year: 2017).*
Machine Translation of JP2006084185A (Year: 2006).*
Machine Translation of 20160011842A (Year: 2016).*
Communication dated Feb. 20, 2020, issued by the Korean Intellectual Property Office in counterpart Korean Application No. 10-2019-0174293.

* cited by examiner

*Primary Examiner* — Joel G Horning
(74) *Attorney, Agent, or Firm* — Sughrue Mion, PLLC (57) ABSTRACT

Provided is a method of inspecting a growth quality of a graphene layer of a graphene-grown copper foil obtained by growing the graphene layer on a copper foil layer by chemical vapor deposition (CVD), the method including reacting oxygen or water molecules with the copper foil layer via a defect portion of the graphene layer, partitioning an entire region of the graphene-grown copper foil into partial regions, sequentially obtaining images of the partial regions, detecting, with respect to each of the images of the partial regions, an oxidized region where the copper foil layer is oxidized, and setting the oxidized region as a graphene defect region, and obtaining a ratio of an area of the graphene defect region to an entire area of each of the images of the partial regions.

6 Claims, 11 Drawing Sheets

METHOD AND SYSTEM FOR INSPECTING GROWTH QUALITY OF GRAPHENE

CROSS-REFERENCE TO THE RELATED APPLICATION

This application claims priority from Korean Patent Application No. 10-2019-0174293, filed on Dec. 24, 2019, in the Korean Intellectual Property Office, the disclosure of which is incorporated herein in its entirety by reference.

BACKGROUND

1. Field

One or more example embodiments relate to a method and system for inspecting growth quality of graphene, and more particularly, to a method and system for inspecting growth quality of graphene of a second layer of a graphene-grown copper foil obtained by growing a second layer of graphene on a first layer of copper foil by chemical vapor deposition (CVD).

2. Description of Related Art

As a method of manufacturing graphene, a chemical vapor deposition (CVD) method is widely used. According to this method, a graphene-grown copper foil is formed as a result of growing a second layer of graphene on a first layer of copper foil by CVD.

In the above-described graphene-grown copper foil, a seed is formed on a surface of the copper foil which is a catalytic metal, and as graphene is grown around the seed, respective graphene domain regions are generated, and domain boundaries where neighboring graphene domain regions are stitched are formed. The copper foil may be removed by stacking a carrier film on the graphene-grown copper foil. Graphene from which the copper foil is removed may be transferred to a target substrate to be used in industrial fields.

Here, a process of inspecting growth quality of graphene in the graphene-grown copper foil is required before the copper foil is removed. According to related art, the copper foil is oxidized via a defect portion of graphene, and then the growth quality of the graphene is inspected by an operator by using a low-power or high-power microscope. As a method of oxidizing a copper foil, a method of applying ultraviolet rays or heat in the air or a method of dropping an aqueous peroxide solution is used.

Figure 1:
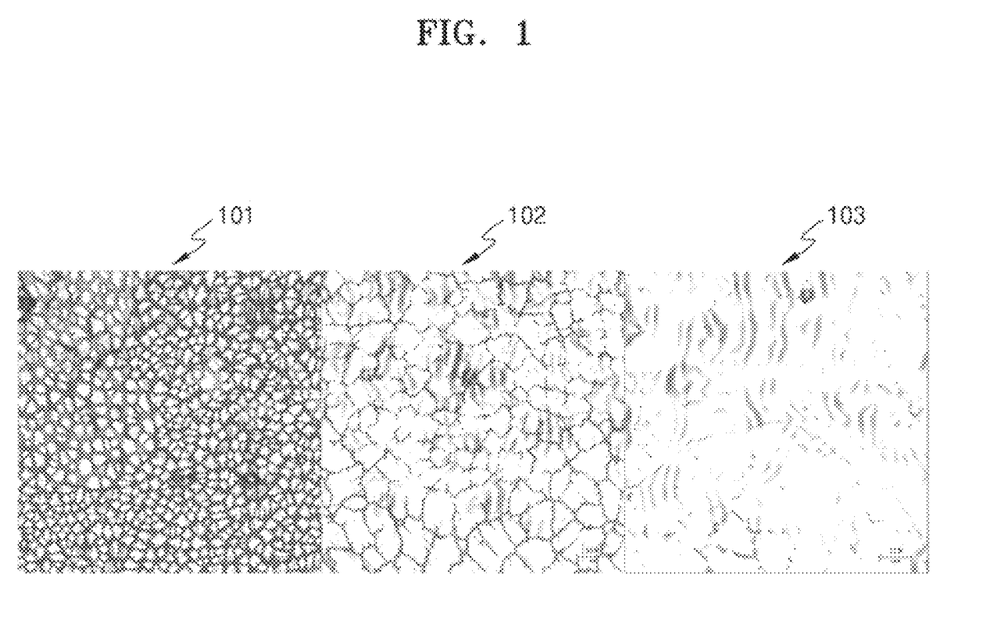
FIG. 1 shows photographic images of oxidized copper foils according to growth qualities of graphene by chemical vapor deposition (CVD) after heat is irradiated to a graphene-grown copper foil at a particular temperature for a certain period of time.

FIG. 1 shows photographic images of oxidized copper foils according to growth qualities of graphene by CVD after heat is irradiated to a graphene-grown copper foil at a particular temperature for a certain period.

FIG. 1 illustrates insufficiently grown graphene 101, incompletely stitched graphene 102, and well-stitched graphene 103.

Referring to FIG. 1, a defect of the graphene 101 due to insufficient growth appears relatively large in graphene domain regions, and thus may be detected using a low-power microscope. A defect of the graphene 102 due to incomplete stitching of domains appears relatively small on a domain boundary, and thus may be detected using a high-power microscope. Accordingly, to more precisely inspect any defects of graphene, a high-power microscope is required. Here, a field of view (FOV) of a low-power microscope is relatively wide, and a FOV of a high-power microscope is relatively narrow.

Thus, according to a manual graphene inspection method according to related art, defects of graphene cannot be quantitatively analyzed, and a state of the entire region of graphene is not effectively monitored.

The background art described above is a technique that the inventor had to derive the present disclosure or technical information acquired during the process of deriving the same, and is not necessarily a technique known to the general public prior to the filing of the present disclosure.

SUMMARY

One or more embodiments include a method and system for inspecting graphene, whereby defects of graphene may be quantitatively analyzed and a state of the entire region of graphene may be more effectively monitored.

Additional aspects will be set forth in part in the description which follows and, in part, will be apparent from the description, or may be learned by practice of the example embodiments.

According to an aspect of an example embodiment, there is provided a method of inspecting a growth quality of a graphene layer of a graphene-grown copper foil obtained by growing the graphene layer on a copper foil layer by chemical vapor deposition (CVD), the method including reacting oxygen or water molecules with the copper foil layer via a defect portion of the graphene layer, partitioning an entire region of the graphene-grown copper foil into partial regions, sequentially obtaining images of the partial regions, detecting, with respect to each of the images of the partial regions, an oxidized region where the copper foil layer is oxidized, and setting the oxidized region as a graphene defect region, and obtaining a ratio of an area of the graphene defect region to an entire area of each of the images of the partial regions.

The partial regions may be uniformly spaced apart in an X-axis direction and a Y-axis direction.

The images of the partial regions may be obtained by an optical microscope along the X-axis and the Y-axis.

The entire area may correspond to an area of a field of view (FOV) of the optical microscope.

When a photographing magnifying power of a camera required to detect the oxidized region is applied, the partial regions respectively may correspond to a field of view (FOV) of the camera.

A well-stitched region of the graphene and the oxidized region of the graphene may be determined based on hue and saturation.

The oxidized region of the copper foil may be detected after removing an image of wrinkles of the copper foil.

According to another aspect of an example embodiment, there is provided a system for inspecting a growth quality of a graphene layer of a graphene-grown copper foil obtained by growing the graphene layer on a copper foil layer by chemical vapor deposition (CVD), the system including an oxidation apparatus configured to cause the copper foil layer to react with oxygen or water molecules via a defect portion of the graphene layer, and an analysis apparatus configured to partition an entire region of the graphene-grown copper foil into partial regions and sequentially obtain images of the partial regions, detect, with respect to each of the images of the partial regions, a region where the copper foil layer is oxidized, and set the oxidized region as a graphene defect region, and calculate a ratio of an area of the graphene defect area to an entire area of each of the images of the partial regions.

The analysis apparatus may include a photographing apparatus and a processing apparatus, wherein the processing apparatus may include a user input/output interface and a computer, wherein the computer is configured to partition the entire region of the graphene-grown copper foil into partial regions and sequentially obtain images of the partial regions by the photographing apparatus, detect, with respect to each of the images of the partial regions, the oxidized region where the copper foil layer is oxidized, and set the oxidized region as a graphene defect region, and calculate the ratio of an area of the graphene defect region to an entire area of each of the images of the partial regions.

When a photographing magnifying power of a camera required to detect the oxidized region is applied, the computer may be further configured to set the partial regions to respectively correspond to a field of view (FOV) of the camera.

The computer may be further configured to determine a well-stitched region of the graphene and the oxidized region of the graphene based on hue and saturation.

The computer may be further configured to detect the oxidized region after removing an image of wrinkles of the copper foil.

The computer may be further configured to set the partial regions to have a uniform interval in an X-axis and a Y-axis direction.

The photographing apparatus may include a suction table configured to adsorb the graphene-grown copper foil, an X-axis stage configured to move the suction table in an X-axis horizontal direction, a Y-axis stage configured to move the suction table and the X-axis stage in a Y-axis horizontal direction, a high-power camera, and a low-power camera.

The computer may be further configured to operate the high-power camera or the low-power camera in synchronization with the X-axis stage and the Y-axis stage based on a number of the partial regions input to the computer by the user input/output interface

BRIEF DESCRIPTION OF THE DRAWINGS

The above and/or other aspects, features, and advantages of example embodiments of the disclosure will be more apparent from the following description taken in conjunction with the accompanying drawings, in which.

DETAILED DESCRIPTION

Reference will now be made in detail to example embodiments of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Figure 2:
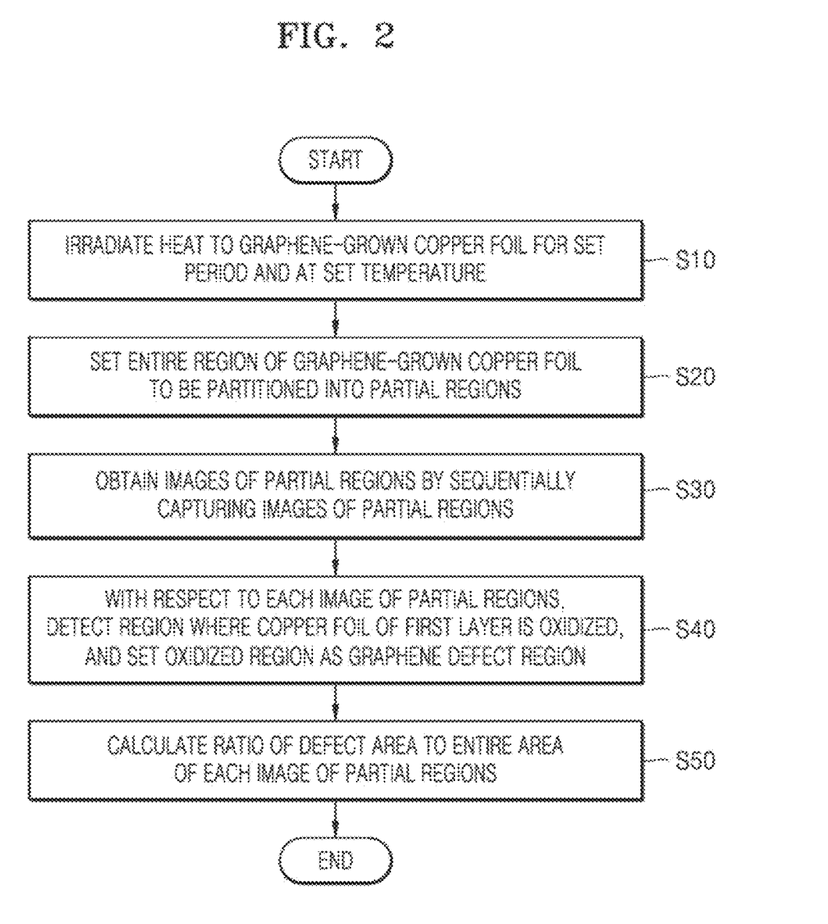
FIG. 2 is a flowchart of a graphene inspection method according to an example embodiment.

FIG. 2 illustrates a graphene inspection method according to an example embodiment.

Figure 3:
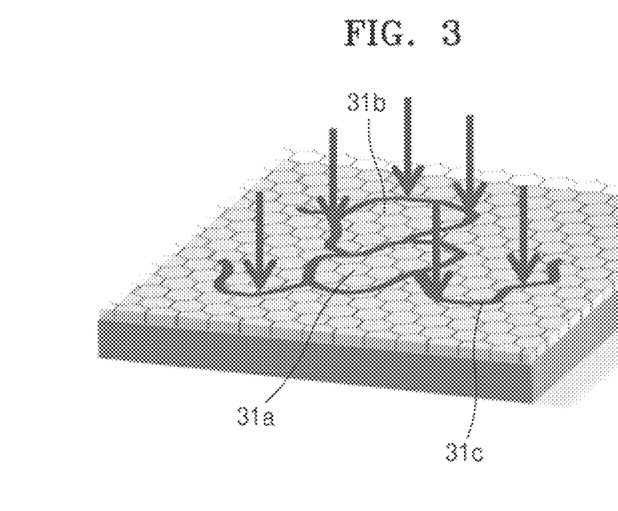
FIG. 3 is a diagram for describing oxidation of a copper foil surface under a domain boundary of graphene in operation (a) of FIG. 2.

FIG. 3 is a diagram for describing oxidation of a copper foil surface under a domain boundary 31c of graphene in operation S10 of FIG. 2.

FIG. 3 illustrates a graphene-grown copper foil 31 obtained by growing graphene on a copper foil by chemical vapor deposition (CVD). In the graphene-grown copper foil 31, as graphene is grown around a seed, graphene domain regions 31a and 31b are formed, and the domain boundary 31c stitching neighboring graphene domain regions is formed.

Figure 4:
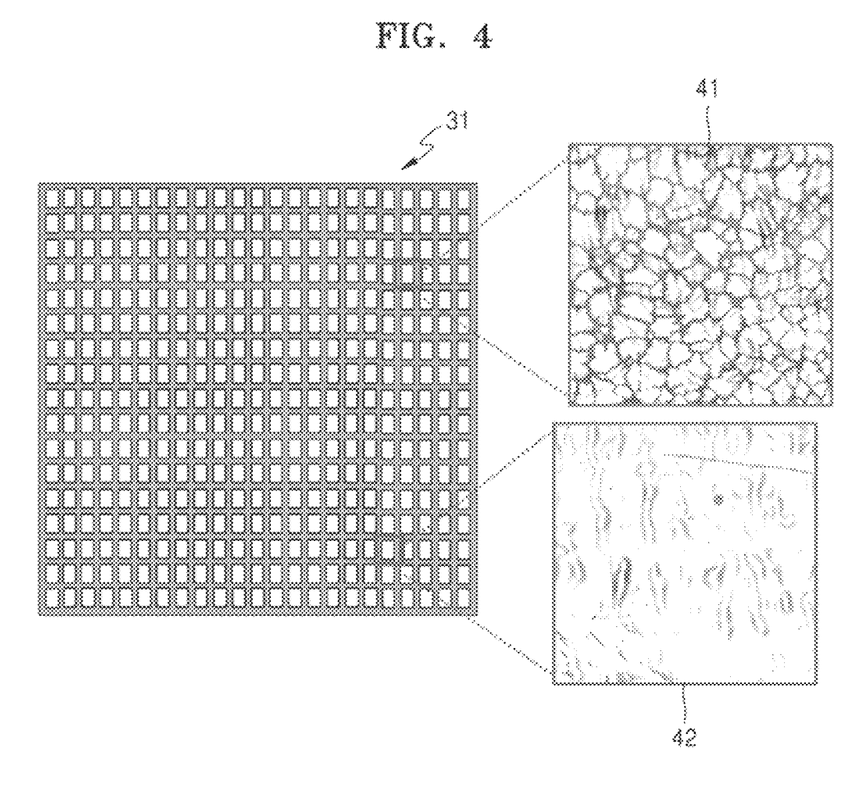
FIG. 4 is a diagram for describing operations (b) and (c) of FIG. 2.

FIG. 4 is a diagram for describing operations S20 and S30 of FIG. 2.

FIG. 4 illustrates partial regions 41 and 42.

Figure 5:
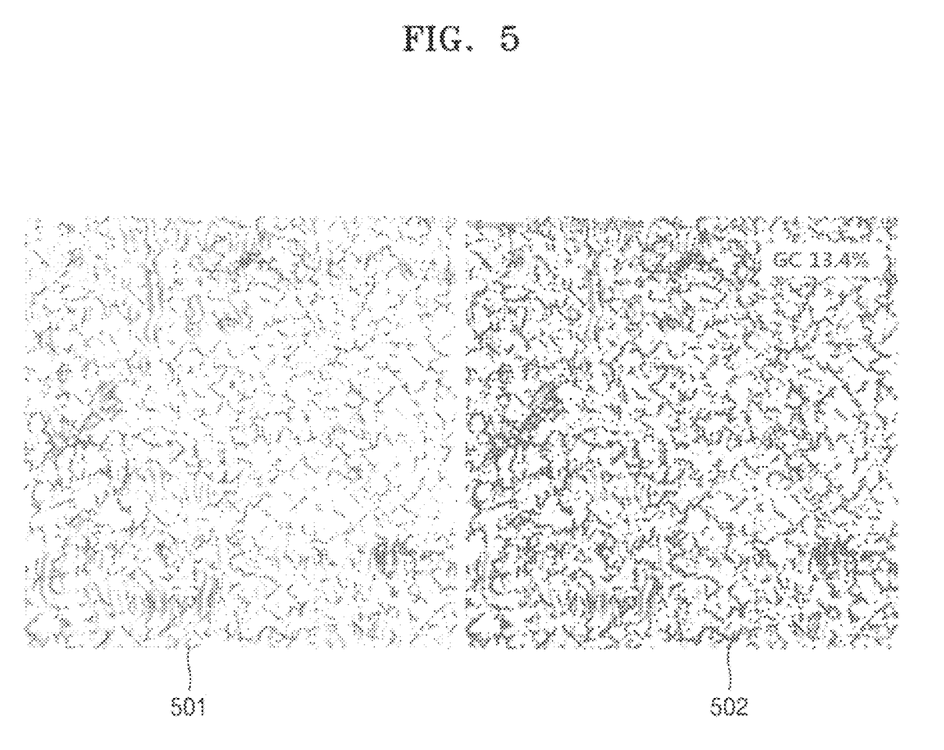
FIG. 5 illustrates calculation of a ratio of a graphene defect area in a photographic image of a partial region of FIG. 4.

FIG. 5 illustrates calculation of a ratio GC of a graphene defect area to a photographic image 501 of a partial region of FIG. 4. FIG. 5 illustrates an image 501 before the ratio GC of the graphene defect area is calculated, and an image 502 after calculating the ratio GC.

The graphene inspection method according to the example embodiment will be described with reference to FIGS. 2 through 5.

Referring to FIG. 2, the method of inspecting graphene according to the example embodiment relates to a method of inspecting growth quality of graphene of a second layer of the graphene-grown copper foil 31 obtained by growing the second layer of graphene on a first layer of a copper foil by CVD.

Initially, by irradiating heat to the graphene-grown copper foil 31 for a set period and at a set temperature, oxygen or water molecules are able to react with the copper foil of the first layer through a defect portion of the graphene of the second layer as illustrated in FIG. 3 (S10).

In a copper foil oxidation method, heat may be irradiated in the air (S10), but embodiments are not limited thereto. For example, ultraviolet rays may also be irradiated in the air. Also, an aqueous peroxide solution may be dropped.

Here, a degree of reaction of the copper foil of the first layer may vary according to the set period and the set temperature. Details regarding the above will be described in detail with reference to FIG. 7. In FIG. 3, moisture or oxygen penetrates into a surface of the copper foil through defects of the domain boundary 31c of the graphene. Accordingly, a copper foil surface under the domain boundary 31c of the graphene will be oxidized. Next, an entire region of the graphene-grown copper foil 31 is set to be partitioned into partial regions as illustrated in FIG. 4 (S20). Here, the partial regions may be set to have an equal area and an equal interval, and thus, images of the partial regions may be more quickly captured sequentially (S30). In addition, when applying a photographing magnifying power of a camera required in detecting the oxidized region in operation S40, the partial regions respectively correspond to a field of view (FOV) of the camera. Accordingly, graphene defect regions may be more quickly detected from the images 41 and 42 of the partial regions by using a photographing apparatus capable of performing scanning along X-Y axes (S40).

The images 41 and 42 of the partial regions are obtained by sequentially capturing images of the partial regions 41 and 42 (S30). As the partial regions respectively have an equal area and an equal interval, the partial regions may be more quickly photographed sequentially.

With respect to each of the images of the partial regions 41 and 42, a region where the copper foil of the first layer is oxidized is detected, and the oxidized region is set as a graphene defect region (S40). Here, a well-stitched region of the graphene and the oxidized region of the graphene are determined by hue and saturation.

In the example embodiment, after removing an image of wrinkles of the copper foil, a region where the copper foil is oxidized is detected. Accordingly, the graphene defect region may be detected more accurately.

For reference, when graphene is grown on a copper foil by CVD, a high-temperature process at 1000° C. or higher is required. Thus, the copper foil which has undergone a high-temperature growth process may have wrinkles due to thermal expansion and contraction. As an image of the wrinkles of the copper foil is similar in shape to the domain boundary of the graphene, the image may act as noise when detecting a graphene defect region.

Therefore, in the example embodiment, for each of the images 41 and 42 of the partial regions, after removing or filtering the image of the wrinkles, a region where the copper foil is oxidized is detected. A method of extracting the image of wrinkles of the copper foil is as follows.

First, from each of the images 41 and 42 of the partial regions, edge images are extracted, and edge images having a lower change rate in a gray scale than a reference value are determined as images of wrinkles of the copper foil. Here, edge images having a gray scale change rate that is higher than a reference value may be domain boundary images of graphene.

Second, an image of wrinkles of the copper foil is determined according to the characteristics of colors such as hue or RGB values.

Reference values to be applied to the two methods may vary depending on photographing conditions such as a light source and illuminance, a state of the graphene-grown copper foil, and characteristics of the camera. That is, the reference values to be applied to the above two methods should be found through experiments based on the purpose of a final application product.

After detecting a region where the copper foil of the first layer is oxidized (S40), for each of the images 41 and 42 of the partial regions, a ratio of the graphene defect area to the entire area, the area of the photographed FOV, is calculated in operation S50. Accordingly, the state of the entire region of the graphene may be more effectively monitored.

Figure 10:
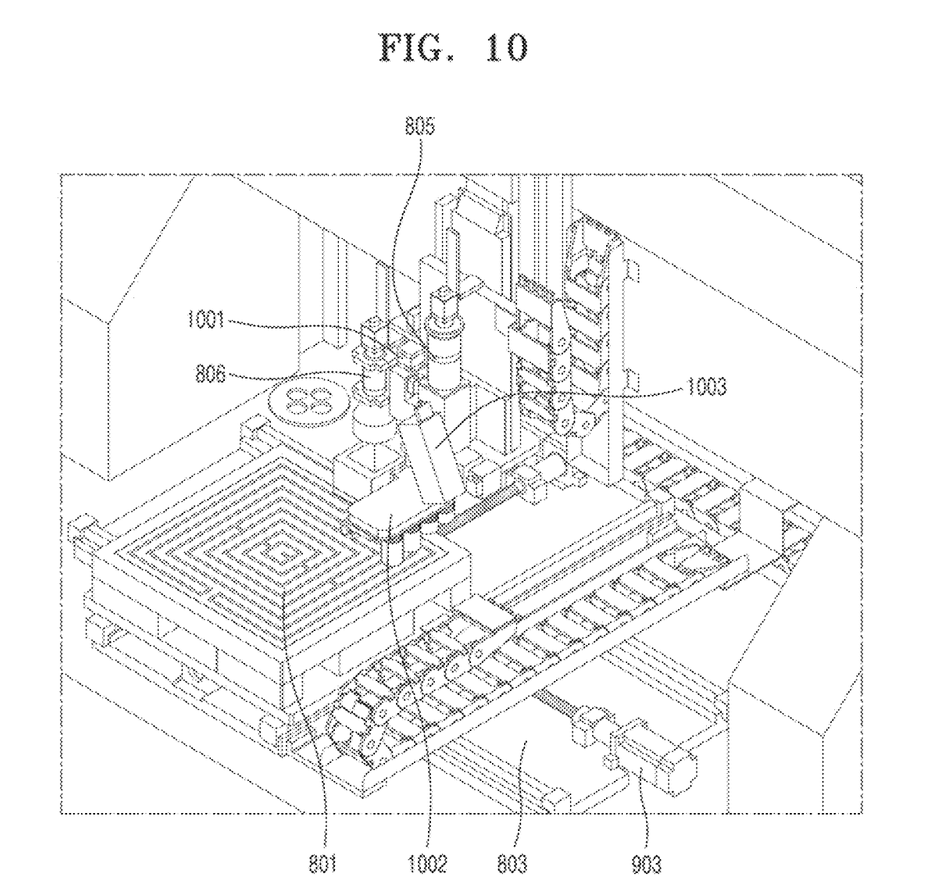
FIG. 10 is an enlarged perspective view of main portions of the photographing apparatus of FIG. 6.
Figure 11:
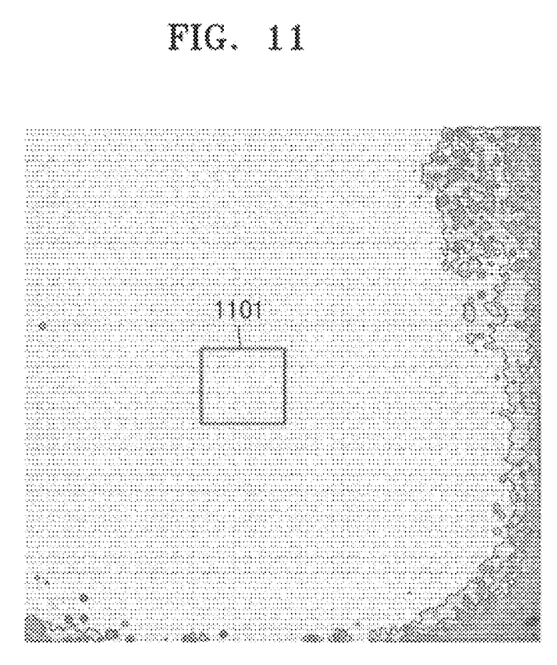
FIG. 11 shows an example of an inspection result according to the inspection system according to the example embodiment.
Figure 12:
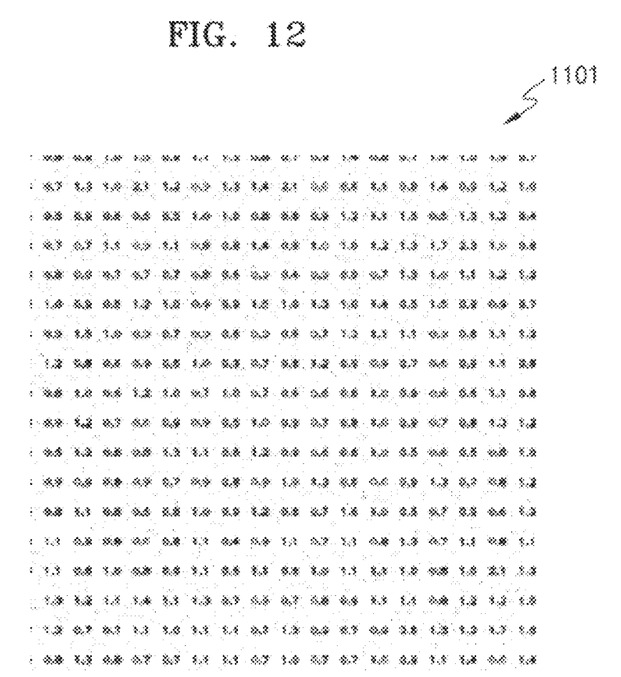
FIG. 12 shows display of a region selected from a screen of FIG. 11 by a user and enlarged.

For example, by setting different colors for each section according to a ratio of the graphene defect area of 0% to 100% and applying the set colors to the ratio of the graphene defect area of the images of the partial regions, a two-dimensional contour map according to the defect ratio to the entire region of the graphene may be displayed as illustrated in FIGS. 10, 11, and 12.

For reference, with respect to an image 502 of any partial region, if an entire area, the area of the photographed FOV, is FV and a graphene defect area is DA, a ratio GC (%) of the graphene defect area is calculated according to Equation 1.

$$GC = \frac{DA}{FV} \times 100 \qquad [\text{Equation 1}]$$

Figure 6:
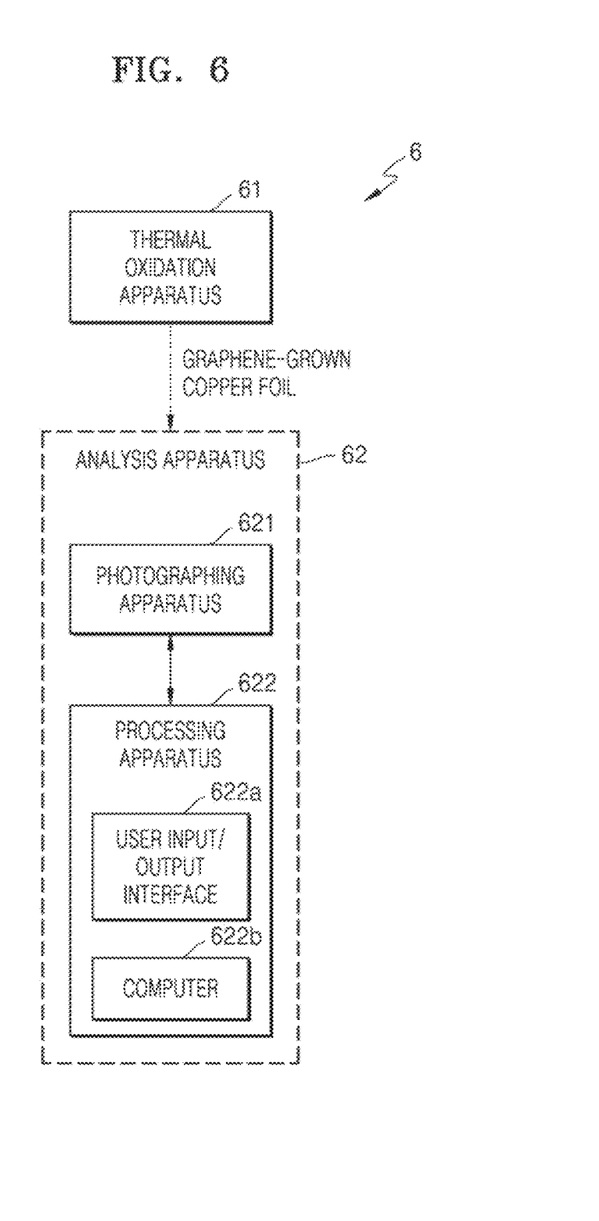
FIG. 6 is a block diagram illustrating a graphene inspection system according to an example embodiment.

FIG. 6 is a block diagram illustrating a graphene inspection system 6 according to an example embodiment. The system of FIG. 6 will be described with reference to FIGS. 3, 4, and 5.

The graphene inspection system 6 according to the example embodiment relates to a system for inspecting growth quality of graphene of the second layer of the graphene-grown copper foil 31 obtained by growing the second layer of graphene on the first layer of the copper foil by CVD. The graphene inspection system 6 includes a thermal oxidation apparatus 61 and an analysis apparatus 62.

The thermal oxidation apparatus 61 makes oxygen or water molecules react with the copper foil of the first layer through a defect portion of the graphene of the second layer by irradiating heat to the graphene-grown copper foil 31 for a set period and at a set temperature. The thermal oxidation apparatus 61 will be described in more detail with reference to FIG. 7.

As described above, in a copper foil oxidation method, heat may be irradiated in the air, but also, a method of irradiating ultraviolet rays may be used. In this case, the graphene inspection system 6 may include an ultraviolet-oxidation apparatus. Also, a method of dropping an aqueous peroxide solution may be used as a copper foil oxidation method. In this case, the graphene inspection system 6 may include a chemical oxidation apparatus.

The analysis apparatus 62 sets an entire region of graphene to be partitioned into partial regions, and obtains the images 41 and 42 of the partial regions by sequentially capturing images of the partial regions.

The analysis apparatus 62 detects a region where the copper foil of the first layer is oxidized, from each of the images 41 and 42 of the partial regions, and sets the oxidized region as a graphene defect region.

The analysis apparatus 62 calculates a ratio of the graphene defect area to the entire area (FOV area) with respect to each of the images 41 and 42 of the partial region.

In detail, the analysis apparatus 62 includes a photographing apparatus 621 and a processing apparatus 622. The processing apparatus 622 includes a user input/output interface 622a and a computer 622b.

The computer 622b sets the entire region of the graphene to be partitioned into the partial regions, and obtains the images 41 and 42 of the partial regions by sequentially capturing images of the partial regions by operating the photographing apparatus 621. Here, when a required photographing magnifying power of the camera required to detect the oxidized region is applied to the photographing apparatus 621, the computer 622b sets each of the partial regions to match the FOV of the camera.

The computer 622b detects a region where the copper foil of the first layer is oxidized, from each of the images 41 and 42 of the partial regions, and sets the oxidized region as a graphene defect region. Here, after removing (filtering) an image of the wrinkles of the copper foil, the computer 622b detects a region where the copper foil is oxidized. In detecting the oxidized region of the copper foil, the computer 622b determines a well-stitched region of the graphene and the oxidized region based on hue and saturation.

The computer 622b calculates a ratio of the graphene defect area to the entire area (FOV area) for each of the images 41 and 42 of the partial regions. Accordingly, the state of the entire region of the graphene may be effectively monitored. For example, the computer 622b may set different colors for each section according to a ratio of the graphene defect area of 0% to 100% according to an input from the user input/output interface 622a, and apply the set colors to the ratio of the graphene defect area of the images 41 and 42 of the partial regions to display a two-dimensional contour map according to the defect ratio to the entire region of the graphene on the user input/output interface 622a as illustrated in FIGS. 10, 11, and 12.

Figure 7:
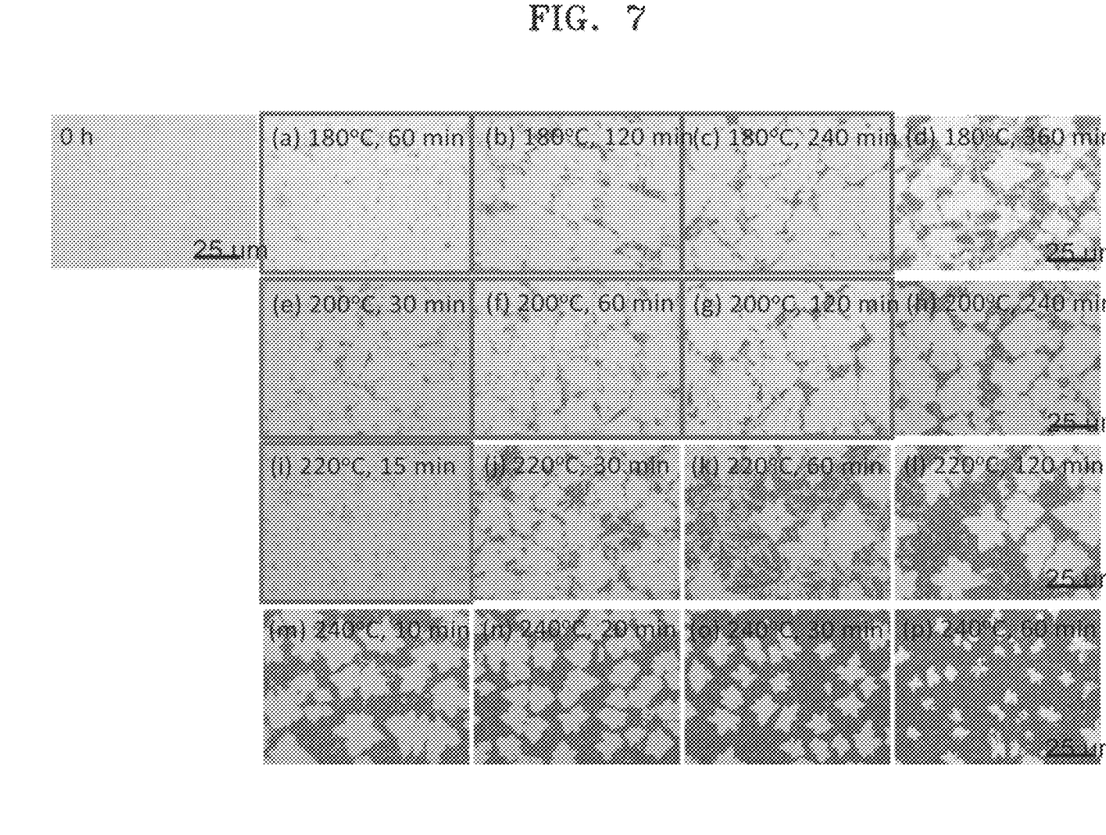
FIG. 7 shows a result of experiments to calculate a heat irradiation period and temperature to be applied to a thermal oxidation apparatus of FIG. 6.

FIG. 7 shows a result of experiments to calculate a heat irradiation period and temperature to be applied to the thermal oxidation apparatus 61 of FIG. 6. In the experiments in the thermal oxidation apparatus 61, different heat radiation periods and temperatures were applied to samples grown under the same conditions.

Referring to FIG. 7, air at 180° C. was irradiated to graphene-grown copper foils (a) through (d) for different periods of time. Air at 200° C. was irradiated to graphene-grown copper foils (e) through (h) for different periods of time. Air at 220° C. was irradiated to graphene-grown copper foils (i) through (l) for different periods of time. Air at 240° C. was irradiated to graphene-grown copper foils (m) through (p) for different periods of time.

According to the results of the experiments, the higher the thermal treatment temperature or the longer the thermal treatment period, the greater the area of the oxidized region. Also, the higher the thermal treatment temperature, the faster the area of the oxidized region was increased.

Accordingly, the heat irradiation period and temperature to be applied in the thermal oxidation apparatus 61 may be set to such an extent that electrical characteristics of a graphene thin film do not greatly vary when the graphene thin film is transferred to a target substrate. According to the results of the experiments of FIG. 7, even by irradiating air at 180° C. for (a) 60 minutes or (b) 120 minutes or (c) 240 minutes, electrical characteristics of the graphene thin film did not vary greatly. Also, even by irradiating air at 200° C. for (e) 30 minutes or (f) 60 minutes or (g) 120 minutes, electrical characteristics of the graphene thin film did not vary greatly. In addition, even by irradiating air at 220° C. for (i) 15 minutes, electrical characteristics of the graphene thin film did not vary greatly.

Figure 8:
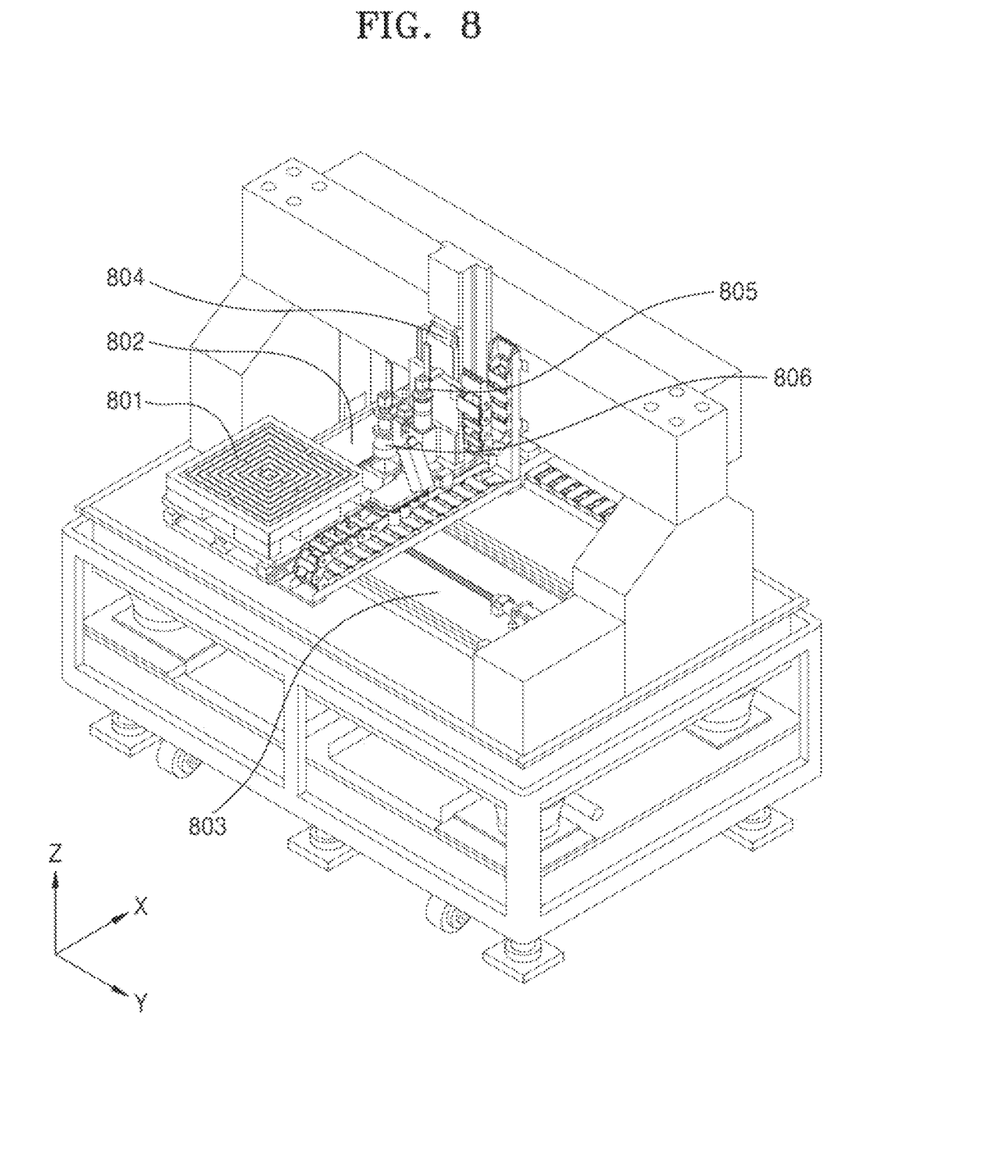
FIG. 8 is a perspective view of a photographing apparatus of FIG. 6.

FIG. 8 illustrates the photographing apparatus 621 of FIG. 6.

Figure 9:
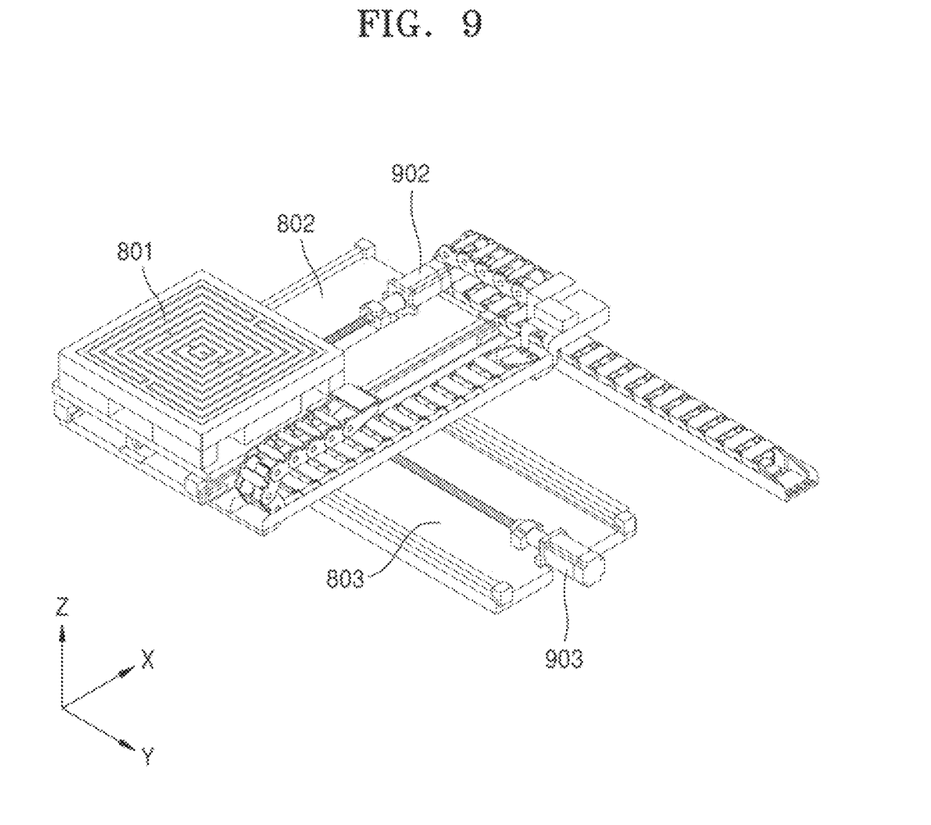
FIG. 9 is a perspective view of a suction table, an X-axis stage, and a Y-axis stage in the photographing apparatus of FIG. 6.

FIG. 9 illustrates a suction table 801, an X-axis stage 802, and a Y-axis stage 803 in the photographing apparatus 621 of FIG. 6. The suction table 801 is formed of a porous material so that a graphene-grown copper foil stretched at a high temperature of 1000° C. or higher may be fixed flatly without curves.

FIG. 10 is an enlarged view of main portions of the photographing apparatus 621 of FIG. 6.

Referring to FIGS. 8, 9, and 10, the photographing apparatus 621 of FIG. 6 includes the suction table 801, the X-axis stage 802, the Y-axis stage 803, a high-power camera 805, and a low-power camera 806.

The suction table 801 that is porous adsorbs a graphene-grown copper foil by using vacuum.

The X-axis stage 802 moves the suction table 801 in an X-axis horizontal direction. The X-axis stage 802 is moved together with the suction table 801 as a stepping motor 902 rotates a ball screw. A resolution of the X-axis stage 802 is 1.0 µm, and a moving speed thereof is 50 mm/sec.

The Y-axis stage 803 moves the suction table 801 and the X-axis stage 802 in a Y-axis horizontal direction as a stepping motor 903 rotates a ball screw. A resolution of the Y-axis stage 803 is 1.0 µm, and a moving speed thereof is 50 mm/sec.

According to the number of partial regions 41 and 42 as illustrated in FIG. 4 input to the computer 622b in FIG. 6 by the user input/output interface 622a in FIG. 6, the computer 622b operates the high-power camera 805 or the low-power camera 806 in synchronization with the X-axis stage 802 and the Y-axis stage 803.

In the example embodiment, a Z-axis stage 804, an auto-focusing motor 1001, a lens changer 1002, and an auto-focus sensor 1003 are further included.

The Z-axis stage 804 moves the high-power camera 805 and the low-power camera 806 vertically. The auto-focusing motor 1001 operates for auto-focusing of the high-power camera 805 and the low-power camera 806 based on a distance sensed by the auto-focus sensor 1003. The lens changer 1002 may change and install objective lenses of different magnifying powers by using a robot function. In the example embodiment, lenses of a magnifying power of 5, 10, 20, and 50 may be used. Lenses of other powers may also be used based on the requirement of the photographing apparatus 621.

FIG. 11 shows an example of an inspection result according to the inspection system 6 in FIG. 6 according to the example embodiment. The inspection result of FIG. 11 is displayed on the user input/output interface 622a in FIG. 6.

FIG. 12 shows display of a region 1101 that is selected from a screen of FIG. 11 by a user and enlarged.

Figure 13:
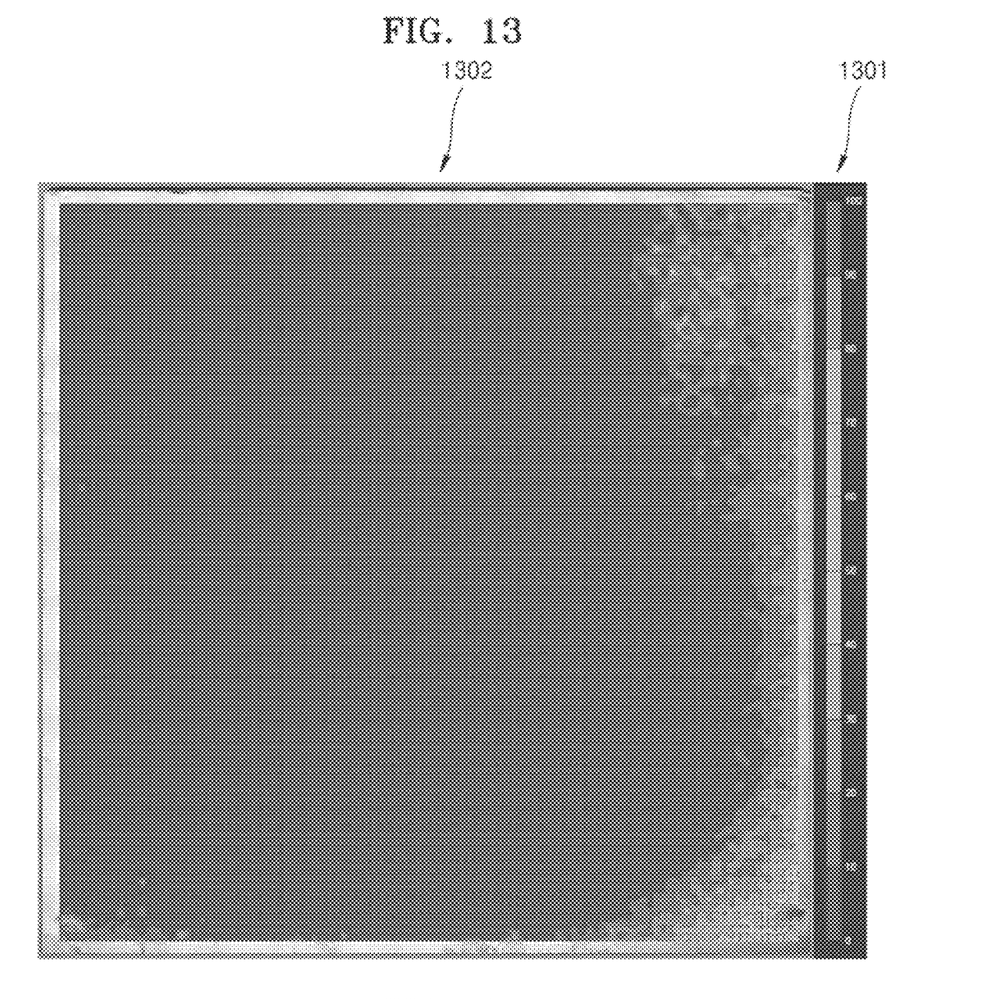
FIG. 13 shows another example of an inspection result according to the inspection system according to the example embodiment.

FIG. 13 shows another example of an inspection result according to the inspection system 6 in FIG. 6 according to the example embodiment. Referring to FIGS. 4 and 11, there are significantly more images of the partial regions of FIG. 11 than the images 41 and 42 of the partial regions of FIG. 4. The number of the images of the partial regions as above is set by an input from the user input/output interface 622a in FIG. 6.

Referring to FIG. 11, a ratio of a graphene defect area to the entire area of the images 41 and 42 of the partial regions is marked by numbers. In addition, as a whole, a contour map according to the ratio of the graphene defect area is formed. The numbers may also be hidden according to choice by a user.

Referring to FIG. 13, a color list 1301 and a contour map 1302 according to each section of growth quality are displayed. That is, by setting different colors for each section according to a ratio of the graphene defect area of 0% to 100% as illustrated in 1301 and applying the set colors to the ratio of the graphene defect area of the images of the partial regions, a two-dimensional contour map as illustrated in 1302 according to the defect ratio to the entire region of the graphene may be displayed.

Thus, according to the result of the inspection as shown in FIG. 11 or 13, a state of the entire region of the graphene may be monitored more effectively.

Figure 14:
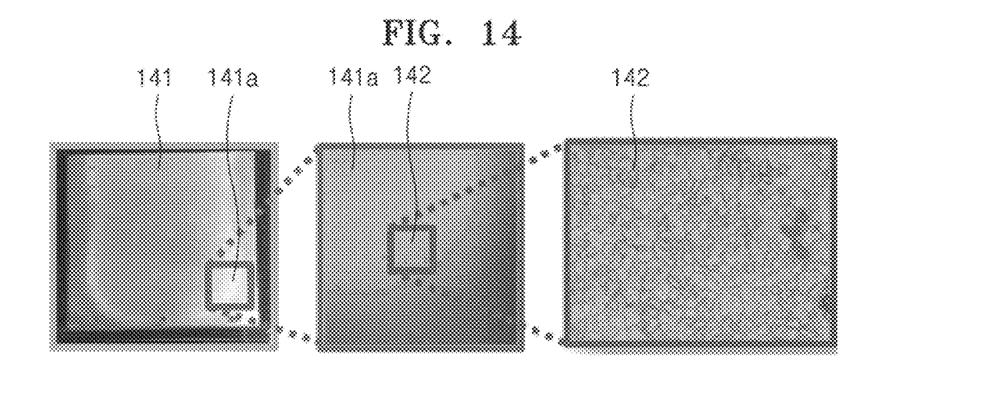
FIG. 14 shows that an oxidized region is detected from a screen of a primary inspection region and that a secondary inspection of the detected, oxidized region is possible.

FIG. 14 shows that an oxidized region 141a is detected from a screen of a primary inspection region 141 and secondary inspection on the detected, oxidized region 141a may be performed.

Referring to FIGS. 6 and 14, results of inspection of FIG. 14 are displayed on the user input/output interface 622a.

For example, the primary inspection region 141 may be a region of a result obtained by quickly performing inspection in a macroscopic manner by using a low-power camera 806 in FIG. 10 in a high-speed inspection mode. The oxidized region 141a may be detected from the primary inspection region 141 based on hue and saturation.

While the primary inspection region 141 and the oxidized region 141a are displayed on the user input/output interface 622a, when a user designates a secondary inspection region 142, the computer 622b may perform a high-resolution inspection mode by using the high-power camera 805 in FIG. 10.

When a high-speed inspection mode or a high-resolution inspection mode is performed as above, the inspection area 141 or 142 is designated by the user input/output interface 622a, and when the number of partial regions is designated, the partial regions partitioned as a result of the designation correspond to a FOV of the high-power camera 805 in FIG. 10. Accordingly, the higher the magnifying power, the narrower the FOV, but the greater the number of partial regions, the more accurate and precisely the growth quality of graphene may be monitored.

In the example embodiment, a 50-power objective lens may be used, and a FOV of the objective lens is a square region having horizontal and vertical lengths of 0.225 mm each may be used. Here, when intervals between the partial regions are set to 3.5 mm, growth quality of graphene with respect to the entire inspection region of the graphene may be more effectively monitored.

As described above, according to the graphene inspection method and system of the example embodiment, when a photographing magnifying power required to detect graphene defect regions is applied, the partial regions respectively correspond to a FOV of a camera. Thus, by using a photographing apparatus capable of performing scanning along X-Y axes, graphene defect regions may be more quickly detected from images of the partial regions. In addition, as the graphene defect regions are more quickly detected, a ratio of a graphene defect area may be more quickly calculated.

Based on the photographed images, a degree of graphene defects may not be quantitatively accurately analyzed. In this regard, in the example embodiment, a ratio of a graphene defect area to the entire area is calculated with respect to each image of the partial regions, and thus, a degree of graphene defects may be quantitatively more accurately analyzed, and a state of the entire region of the graphene may be more effectively monitored.

For example, by setting different colors for each section according to a ratio of the graphene defect area of 0% to 100% and applying the set colors to the ratio of the graphene defect area of the images of the partial regions, a two-dimensional contour map according to the defect ratio to the entire region of the graphene may be displayed.

It should be understood that example embodiments described herein should be considered in a descriptive sense only and not for purposes of limitation. Descriptions of features or aspects within each example embodiment should typically be considered as available for other similar features or aspects in other embodiments. While example embodiments have been described with reference to the figures, it will be understood by those of ordinary skill in the art that various changes in form and details may be made therein without departing from the spirit and scope of the disclosure as defined by the following claims.

What is claimed is:

1. A method of inspecting a growth quality of a graphene layer of a graphene-grown copper foil obtained by growing the graphene layer on a copper foil layer by chemical vapor deposition (CVD), the method comprising:
   reacting oxygen or water molecules with the copper foil layer via a defect portion of the graphene layer;
   partitioning an entire region of the graphene-grown copper foil into partial regions;
   sequentially obtaining images of the partial regions of the graphene layer, wherein at least one of the images of the partial regions shows the graphene layer comprising one or more domain boundaries and one or more wrinkles of the copper foil layer, wherein the domain boundaries in the graphene layer are at a surface of the graphene-grown copper foil, and wherein the one or more wrinkles of the copper foil layer are below the surface of the graphene-grown copper foil;
   for each image including the one or more wrinkles, comparing gray scale change rates in the image to a reference value, wherein a first set of gray scale change rates in the images having values lower than the reference value are attributable to the one or more wrinkles, and wherein a second set of the gray scale change rates in the images having values higher than the reference value are attributable to the one or more domain boundaries;
   removing or filtering the one or more wrinkles of the copper foil layer by removing or filtering the grey scale change rates of which the values are lower than the reference value, leaving the one or more domain boundaries shown in the at least one of the images;
   after the removing or filtering, detecting, with respect to each of the images of the partial regions, an oxidized region where the copper foil layer is oxidized, and setting the oxidized region as a graphene defect region; and
   obtaining a ratio of an area of the graphene defect region to an entire area of each of the images of the partial regions.

2. The method of claim 1, wherein the partial regions are uniformly spaced apart in an X-axis direction and a Y-axis direction.

3. The method of claim 2, wherein the images of the partial regions are obtained by an optical microscope along the X-axis and the Y-axis.

4. The method of claim 3, wherein the entire area corresponds to an area of a field of view (FOV) of the optical microscope.

5. The method of claim 1, wherein when a photographing magnifying power of a camera required to detect the oxidized region is applied, the partial regions respectively correspond to a field of view (FOV) of the camera.

6. The method of claim 1, wherein non-oxidized region of the graphene layer and the oxidized region of the graphene layer are determined based on hue and saturation.

\* \* \* \* \*